US009588061B2

(12) United States Patent
Sun et al.

(10) Patent No.: US 9,588,061 B2
(45) Date of Patent: Mar. 7, 2017

(54) MEASURING WHISPERING-GALLERY-MODE RESONATOR

(71) Applicants: Institute of Physics, Chinese Academy of Sciences, Beijing (CN); Beijing Huarong Tianchuang Superconduct Technology Development Co., Ltd, Beijing (CN); University of Science and Technology Beijing, Beijing (CN); O. Ya. Institute for Radiophysics and Electronics of National Academy of Sciences of Ukraine, Kharkiv (UA)

(72) Inventors: Liang Sun, Beijing (CN); Xu Wang, Beijing (CN); Jia Wang, Beijing (CN); Yun Wu, Beijing (CN); Yusheng He, Beijing (CN); Hong Li, Beijing (CN); Jiangming Huang, Beijing (CN); Sheng Luo, Beijing (CN); Mykola Cherpak, Kharkiv (UA); Valerii Skresanov, Kharkiv (UA); Oleksandr Barannyk, Kharkiv (UA); Volodymyr Glamazdin, Kharkiv (UA); Oleksandr Shubny, Kharkiv (UA)

(73) Assignees: Institute of Physics, Chinese Academy of Sciences, Beijing (CN); Beijing Huarong Tianchuang Superconduct Technology Development Co., Ltd., Beijing (CN); University of Science and Technology Beijing, Beijing (CN); O. YA. Institute For Radiophysics and Electronics of National Academy of Sciences of Ukraine, Kharkiv (UA)

( * ) Notice: Subject to any disclaimer, the term of this patent is extended or adjusted under 35 U.S.C. 154(b) by 326 days.

(21) Appl. No.: 14/195,578

(22) Filed: Mar. 3, 2014

(65) Prior Publication Data

US 2014/0247061 A1 Sep. 4, 2014

(30) Foreign Application Priority Data

Mar. 4, 2013 (UA) .................................. 201302666

(51) Int. Cl.
*G01N 22/00* (2006.01)
*G01S 13/89* (2006.01)
(Continued)

(52) U.S. Cl.
CPC ........... *G01N 22/00* (2013.01); *G01F 23/284* (2013.01); *G01R 27/04* (2013.01); *G01S 13/88* (2013.01); *G01S 13/89* (2013.01)

(58) Field of Classification Search
CPC ....... G01F 23/284; G01N 22/00; G01S 13/88; G01S 13/89; G01R 27/04
(Continued)

(56) References Cited

U.S. PATENT DOCUMENTS 4,918,049 A * 4/1990 Cohn ...................... H01J 23/20
315/4
4,968,945 A * 11/1990 Woskov ................. H01J 23/20
324/633
(Continued)

FOREIGN PATENT DOCUMENTS

UA 16620 U 8/2006

OTHER PUBLICATIONS

Charles Wilker, Zhi-Yuan Shen, Viet Nguyen, & Michael Brenner; (A Sapphire Resonator for Microwave Characterization of Superconducting Thin Films; ARFTG Conference Digest-Spring, 41st (vol. 23) Jun. 1993; pp. 38-47; DOI:10.1109/ARFTG.1993. 327018; Publisher: IEEE).*
(Continued)

*Primary Examiner* — Jermele M Hollington
*Assistant Examiner* — Christopher McAndrew
(74) *Attorney, Agent, or Firm* — Knobbe, Martens, Olson & Bear LLP

(57) ABSTRACT

A measuring whispering-gallery-mode resonator includes: a dielectric resonating body with a rotation axis, a superconducting sample under test mounted to the resonating body and a coupling unit for coupling a measuring waveguide with the resonating body. One side of the resonating body connected with the coupling unit has a first endplate, in which m coupling holes penetrate through the first endplate, and centers of the m coupling holes are arranged to be evenly spaced along a circle whose center is on the rotation axis. The coupling unit has a feeder line which is a coaxial waveguide, and an axis of the coaxial waveguide coincides with the rotation axis. One end surface of the coaxial waveguide, which is perpendicular to the rotation axis, abuts the first endplate; and the azimuth index of operated whispering gallery mode in the resonator is an integer multiple of the number m of the coupling holes.

11 Claims, 8 Drawing Sheets

(51) Int. Cl.
  G01F 23/284 (2006.01)
  G01S 13/88 (2006.01)
  G01R 27/04 (2006.01)

(58) Field of Classification Search
  USPC ........................................................ 324/642
  See application file for complete search history.

(56) References Cited

U.S. PATENT DOCUMENTS

| | | | | |
|---|---|---|---|---|
| 5,231,073 A | * | 7/1993 | Cohn | H01J 23/20 |
| | | | | 264/322 |
| 5,909,160 A | * | 6/1999 | Dick | H01P 7/10 |
| | | | | 331/96 |
| 6,501,972 B1 | * | 12/2002 | Carlsson | H01P 7/082 |
| | | | | 333/219 |
| 6,988,058 B1 | * | 1/2006 | Sherwin | B82Y 10/00 |
| | | | | 250/207 |
| 7,292,112 B2 | * | 11/2007 | Oxborrow | H01P 7/10 |
| | | | | 331/96 |
| 2007/0001773 A1 | * | 1/2007 | Oxborrow | H01P 7/10 |
| | | | | 331/154 |
| 2009/0295510 A1 | * | 12/2009 | Miyazaki | B82Y 20/00 |
| | | | | 333/219.2 |

OTHER PUBLICATIONS

Krupka, Jerzy; Mazierska, Janina; (Single-crystal dielectric resonators for low-temperature electronics applications; IEEE Transactions on Microwave Theory and Techniques (vol. 48 , Issue: 7 ); pp. 1270-1274, Date of Publication: Jul. 2000).*

B.N. Das, P. V. D. Somasekhar; (Analysis of a transition between rectangular and circular waveguides; IEEE Transactions on Microwave Theory and Techniques (vol. 39 , Issue: 2 ); pp. 357-359); Date of Publication: Feb. 1991.).*

Cherpak, et al. 2003 "Accurate Microwave Technique of Surface Resistance Measurement of Large-area HTS Films using Sapphire Quasioptical Resonator" *IEEE Transactions on Applied Superconductivity* 13(2): 3570-3573.

Cherpak, et al. 2004 "Microwave Impedance characterization of large-area HTS films: a novel approach" *Superconductivity Science and Technology* 17(7): 899-903.

Ginsberg, 1996, in Physical Properties of High Temperature Superconductors, vol. V; *World Scientific*: pp. 12-15.

Mazierska, et al. 2001 "Accuracy issues in Surface Resistance Measurements of High Temperature Superconductors using Dielectric Resonators" *IEEE Trans. Appl. Supercond* 11(4): 4140-4147.

Shen, 1994, in High-Temperature Superconducting Microwave Circuits,: *Artech House*, Boston-London: pp. 34-43.

* cited by examiner

MEASURING WHISPERING-GALLERY-MODE RESONATOR

CROSS-REFERENCE TO RELATED APPLICATION

This application claims the benefit of Ukraine Patent Application No. a 2013 02666 filed on Mar. 4, 2013 in the Patent Office of Ukraine, the whole disclosure of which is incorporated herein by reference.

BACKGROUND OF THE INVENTION

Field of the Invention

The present invention belongs to the field of microwave technique, in particular to the measurement technique for determination of superconductor surface impedance in millimeter and sub-millimeter wavelength ranges.

Description of the Related Art

Accuracy and sensitivity of substance microwave properties measurement depend on quality (Q)-factor of the resonator. Important peculiarity of the resonator is possibility to measure samples in the forms of small ones or thin films without their pretreatment. In case of studying high temperature superconductors (HTS), measurements of HTS film microwave properties depend on amplitude of the microwave field, i.e. measurements of HTS nonlinear properties are very important.

Conductors including superconductors are characterized by the microwave surface impedance $Z_S=R_S+jX_S$, where $R_S$ is the surface resistance and $X_S$ is the surface reactance. Measurement of surface impedance $Z_S$ is a technical task to determine the microwave properties of superconductors, and a research task in a measurement technique for studying electron system in the above mentioned materials.

Measurement of the surface resistance $R_S$ of the superconductor is a difficult task, because its value is very small. For example, even in Ka-band at liquid nitrogen temperature (77 K) $R_S$=5-7 Ohms for high-temperature superconductor YBa2Cu3O7-δ. By increasing the frequency, $R_S$ increases as the square of frequency ($f^2$), what indicates possibility to increase sensitivity of measurement at the higher frequencies. Unlike normal conductors with normal skin effect, for all superconductors the surface reactance is unequal to the surface resistance and must be measured also [Physical Properties of High Temperature Superconductors V, Editor Donald M. Ginsberg//World Scientific Publishing Co. 1996, 471 p].

With respect to the superconductors, even if surface reactance $X_S$ thereof is larger than surface resistance, and at temperatures significantly below the critical one, $X_S \gg R_S$, $X_S$ remains a small quantity. Nonlinear impedance properties of superconductors, when the surface impedance is a function of the intensity of the microwave field or its power, have great scientific and practical importance.

For the purpose of measurement and study of the superconductor microwave impedance properties, resonator methods are commonly used because they provide greater sensitivity and accuracy. As a rule, the value of Q-factor and resonant frequency of the resonator are measured at weak coupling of feeder lines with the resonator, and the value of Q-factor and resonant frequency of the resonator are close to the resonator eigen characteristics. Q-factor and resonant frequency contain information about electrophysical characteristics of the sample [Zhi-Yuan Shen, High-Temperature Superconducting Microwave Circuits.—Boston-London: Artech House, 1994, 272 p.]. The difference between the known methods is only in the types of resonators used, forms of samples, ways of their placement in the resonator and methodology of study.

When measuring the nonlinear properties of superconductors, it is important to strengthen coupling of the resonator with transmission feeder lines. Here it is necessary to know the value of a coupling coefficient in order to find the resonator eigen Q-factor.

Usually, the same resonators are used to measure $R_S$ and $X_S$. The most important characteristics of all methods of impedance properties measurement are their accuracy and sensitivity. Both properties depend on, which part of the total losses in the resonator are the energy losses in superconductors (i.e., in the sample under test). The energy losses are very small in superconductors compared with losses in normal metals, so normal metals are desirable to exclude completely.

For developing measurement technique of microwave surface resistance, cylindrical dielectric resonators with conducting endplates excited with lower modes have been suggested. Superconducting films on a dielectric substrates were such conducting endplates [Mazierska J. and Wilker Ch. Accuracy issues in Surface Resistance Measurements of High Temperature Superconductors using Dielectric Resonators (corrected), IEEE Trans. Appl. Supercond. —2001.-vol. 11, N° 4.—P.4140-4147]. The abovementioned films are the subject of measurement.

The disadvantage of this device is the practical impossibility to use the dielectric resonator with lower modes in the millimeter and sub-millimeter wavelength ranges through excessive reduction in the size of the resonator and the associated difficulty of effective coupling of the cavity with transmission lines, which further reduces the accuracy and sensitivity of the measurement method.

The mentioned drawback is eliminated in the measuring whispering-gallery-mode resonator, which contains the sample under study and presents a dielectric cylindrical disk as resonating body with one or two flat bases perpendicular to the axis of rotation, in which the endplates of material with high electrical conductivity are installed, and which is equipped with a coupling unit containing a transition from rectangular standard waveguide to the feeder line in the form of dielectric waveguide [Cherpak N, Barannik A, Prokopenko Yu, Filipov Yu, Vitusevich S. Accurate Microwave Technique of Surface Resistance Measurement of Large-area HTS Films using Sapphire Quasioptical Resonator// IEEE Trans. on Appl. Supercond.—2003.-vol. 13, N° 2.—P. 3570-3573]. The resonator is excited with higher modes, namely, whispering gallery modes. The device allows measuring also the temperature dependence of the surface reactance of superconducting films [Cherpak N. T., Barannik A. A., Prokopenko Yu. V., Vitusevich S. A. Microwave Impedance characterization of large-area HTS films; Novel Approach, Superconductivity Science and Technology, vol. 17, N° 7, p. 899-903, 2004].

The disadvantage of this device is the need to use two films in one act of measurement, so the number of acts of measuring individual characteristics of films increases.

The closest analogue on the technical essence is the measuring whispering-gallery-mode resonator, which contains the sample under study, presents a dielectric resonating body with one or two flat bases perpendicular to the axis of rotation, in which the endplates of material with high electrical conductivity are installed, and which is equipped with a coupling unit containing a transition from rectangular standard waveguide to the feeder line of the coupling unit

[Device for measurement of superconductor surface impedance//Barannyk O. A., Bunyaev S. O., ProkopenkoYu. V., Filipov Yu. F., Cherpak M. T. Declarative patent for utility model, UA, 16620U, G01R 27/04, 2006]. The measuring resonator is intended for measurement of microwave surface impedance of superconductors, which are made in the form of endplates of high conductive materials. For the purpose of measuring the individual characteristics of the film in a single act of measurement, the measuring resonator is made as a dielectric resonating body, one of the bases of which abuts to the endplate, which is the superconductor film under test.

In the resonator, whispering gallery modes are excited, so one can increase the size of the resonator in the millimeter wavelength range. The coupling unit of the measuring resonator with a transition from standard rectangular metallic waveguide to the feeder line of coupling unit is made in the form of dielectric waveguide, located near the lateral surface of the dielectric body. The dielectric and metal rectangular waveguides are connected by smooth waveguide transition (or junction).

The advantage of this device is the ability of impedance measurements of superconductors in the millimeter and sub-millimeter wave ranges.

A major shortcoming of the prototype, as well as other above-mentioned measuring resonators with whispering gallery modes, is a technical solution to the coupling units, which degrades performance of the measuring resonator as a whole. Electromagnetic coupling between an open dielectric waveguide and measuring open dielectric resonator is due to the presence of area in space, where the fields of a resonator and a waveguide overlap. In the case of open systems (due to the availability of coupling with space), this leads to two effects: 1) the field of the resonator is scattered by the waveguide, thereby reducing the eigen Q-factor of the resonator, 2) a traveling-wave field of dielectric waveguide is scattered by the resonator into space, thus reducing the efficiency of energy transfer into the resonator. These two effects appear the stronger, the closer are placed together the waveguide and the resonator. Consequence of the above-mentioned effects is the deterioration of the signal-to-noise ratio of measurement system and the existence of systematic (methodical) measurement errors. The signal-to-noise ratio decreases due to the fact that the dielectric waveguide and the measuring resonator are moved away to a distance where the scattering of the resonator field can be neglected. In this case, the signal level is low due to the decrease of the coupling coefficient. In addition, the signal-to-noise ratio decreases due to the fact that the non-resonant radiation signal from the input waveguide and the useful signal from the resonator, which are comparable in the amplitude, interfere in the output waveguide.

At large distances the effect of resonant scattering can be neglected, but the coupling coefficient between the waveguide and measuring resonator thus becomes small, which in turn leads to a decrease in signal-to-noise ratio of the measurement system as a whole. Effect of non-resonant radiation from dielectric waveguide leads to electrodynamic connection between the input and output waveguides, which causes interference effects in the output waveguide between signal of non-resonant radiation and useful signal, which complicates the procedure of tuning the measuring resonator, and also reduces the signal-to-noise ratio. Effect of non-resonant radiation at large distances between the waveguide and the resonator can not be neglected, because power non-resonant radiation can be comparable to the power of the signal.

SUMMARY OF THE INVENTION

The present invention has been made to overcome or alleviate at least one aspect of the above mentioned disadvantages.

As the basis of the invention, the authors set the task of improving a measuring whispering-gallery-mode resonator (hereinafter referred to as resonator) by introducing hitherto unknown coupling unit for the resonator with transmission feeder lines, which would allow increasing the coupling coefficient of the coupling unit adapted to the selected whispering gallery mode at extremely low levels of resonant scattering and non-resonant radiation. This allows a significant increasing in the signal-to-noise ratio and achieving the previously unavailable opportunity to measure the characteristics of the resonator by waves reflected from the resonator. The waves reflected from the resonator, as it is known, enable correct account of the external resonator losses in coupling unit and, thus, allow reducing the systematic error of measuring the characteristics of material of the sample by means of the resonator method and enables measurements of the surface impedance of superconductors in the short-wavelength part of the millimeter-wave and sub-millimeter wave range.

According to an exemplary embodiment of the present invention, a measuring whispering-gallery-mode resonator is provided. The resonator comprises: a dielectric resonating body with a rotation axis; a superconducting sample under test, which is mounted to the resonating body; a coupling unit for coupling a measuring waveguide with the resonating body, wherein one side of the resonating body connected with the coupling unit is provided with a first endplate, wherein m coupling holes penetrate through the first endplate, and centers of the m coupling holes are arranged to be evenly spaced along a circle whose center is on the rotation axis; the coupling unit has a feeder line which is a coaxial waveguide, wherein an axis of the coaxial waveguide coincides with the rotation axis, and one end surface of the coaxial waveguide, which is perpendicular to the rotation axis, abuts to the first endplate; and the azimuthal index of operated whispering gallery mode in the resonator is an integer multiple of the number m of the coupling holes.

Alternatively, the first endplate is made of high conducting material.

Alternatively, the coaxial waveguide is divided in m waveguide sections which have rotational symmetry of the m-th order; and each waveguide section contains a corresponding coupling hole.

Alternatively, the first endplate is made of high conducting material.

Alternatively, the coaxial waveguide is divided into m waveguide sections which have rotational symmetry of the m-th order; and each waveguide section contains a corresponding coupling hole.

BRIEF DESCRIPTION OF THE DRAWINGS

The above and other features of the present invention will become more apparent by describing in detail exemplary embodiments thereof with reference to the accompanying drawings, in which.

DETAILED DESCRIPTION OF PREFERRED EMBODIMENTS OF THE INVENTION

Figure 1:
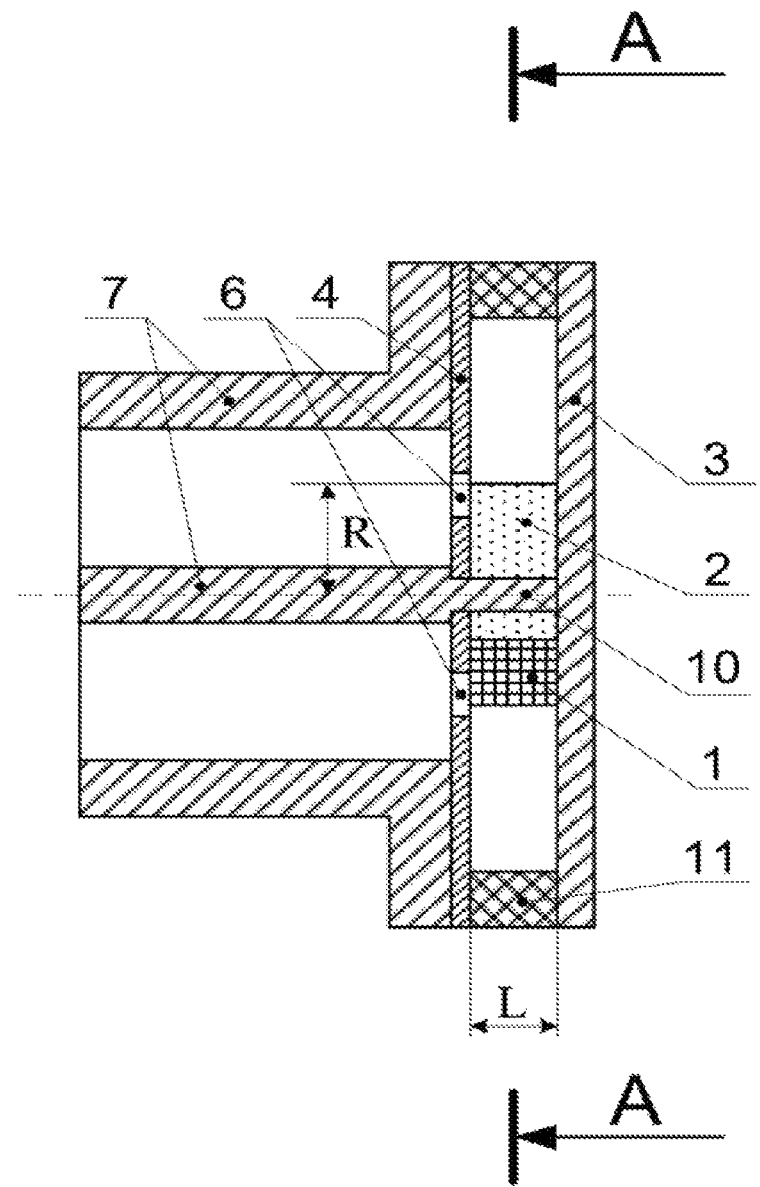
FIG. 1 is a schematic view showing a measuring whispering-gallery-mode resonator according to an exemplary embodiment of the present invention.
Figure 2:
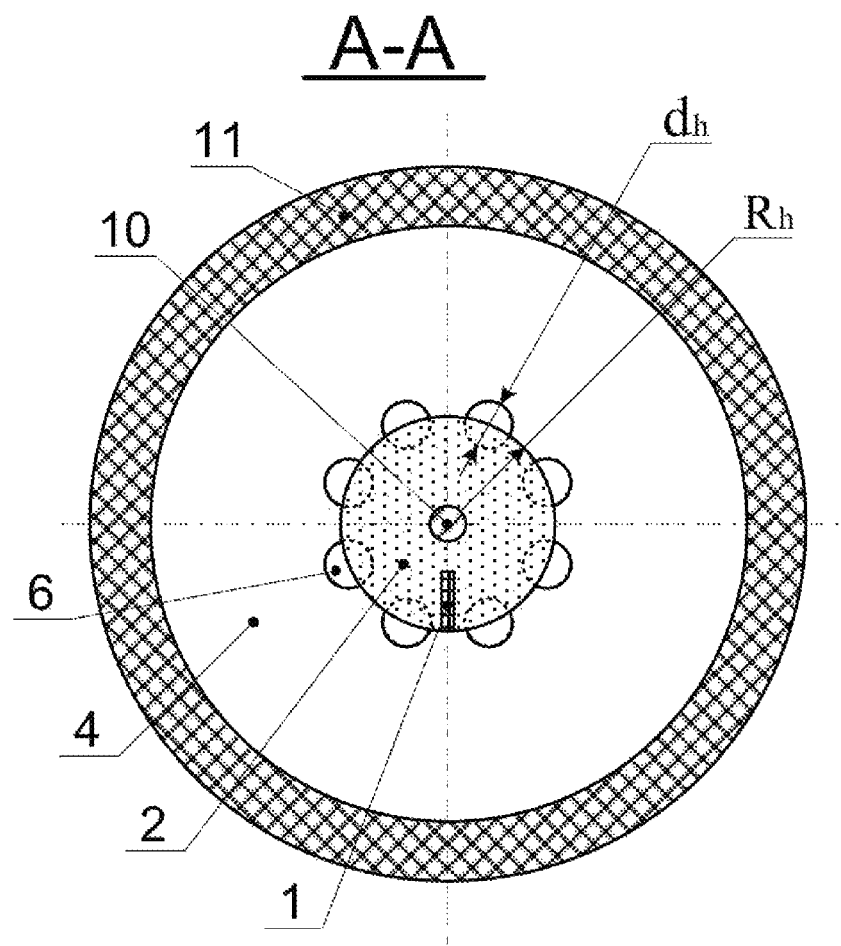
FIG. 2 is an A-A sectional view of the resonator in FIG. 1.

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

According to an exemplary embodiment of the present invention, a measuring whispering-gallery-mode resonator (hereinafter referred to as resonator), which contains the sample 1 under study, comprises a dielectric resonating body 2 with one or two flat bases perpendicular to an axis of rotation thereof, for example, the endplates 3 and 4 of material with high electrical conductivity are installed to the resonating body 2. In some cases of using the resonator, as shown in FIG. 1, an endplate 3 may be the sample 1, which is made of material that is studied, for example, the endplate 3 may be a high-temperature superconducting film. The resonator is equipped with a coupling unit containing a transition from rectangular standard waveguide 5 to the feeder line of the coupling unit.

The endplate 4 may be made in the form of a thin diaphragm, and m coupling holes 6 penetrate through the endplate 4, wherein centers of the m coupling holes 6 are arranged to be evenly spaced along a circle whose center is on the rotation axis. The coupling holes 6 provide electromagnetic coupling of the resonator with the feeder line of the coupling unit. The feeder line of the coupling unit is designed as a coaxial waveguide 7, wherein an axis of the coaxial waveguide coincides with the rotation axis, and one end surface of the coaxial waveguide, which is perpendicular to the rotation axis, abuts to the diaphragm, and the axial index of operating whispering gallery mode in the resonator is an integer multiple of the number m of the coupling holes 6.

Coaxial waveguide 7 is divided by the metal walls into m waveguide sections 8 so that the totality of the waveguide sections 8 has a rotational symmetry of the m-th order. The end surface of the waveguide section 8 of the coaxial waveguide, which is perpendicular to the rotation axis, abuts to the diaphragm (endplate 4), and each section 8 contains a coupling hole 6.

Figure 3:
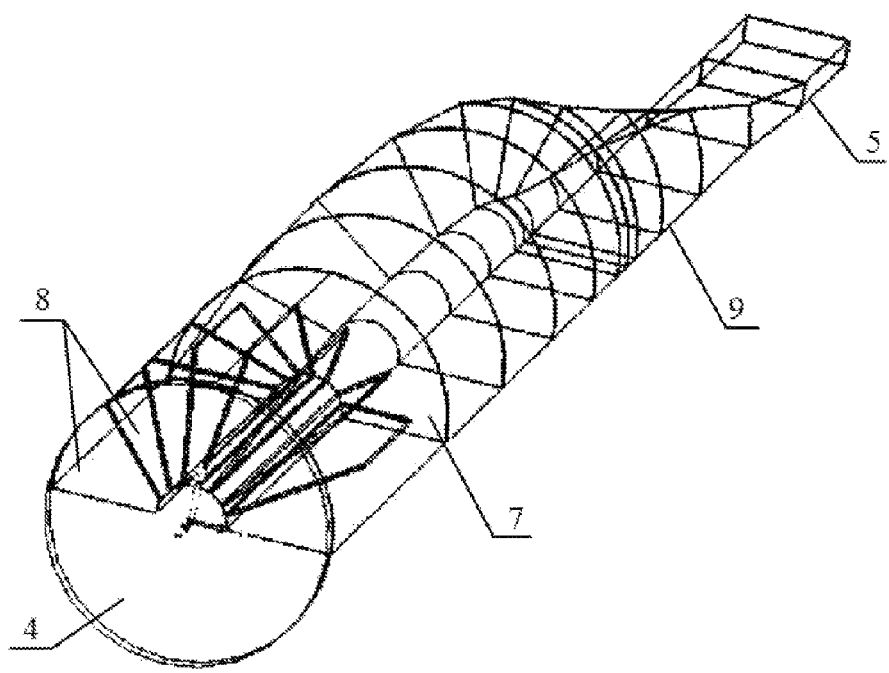
FIG. 3 is a schematic view showing a half section of a transition from a rectangular waveguide to a coaxial waveguide divided into sections.
Figure 4:
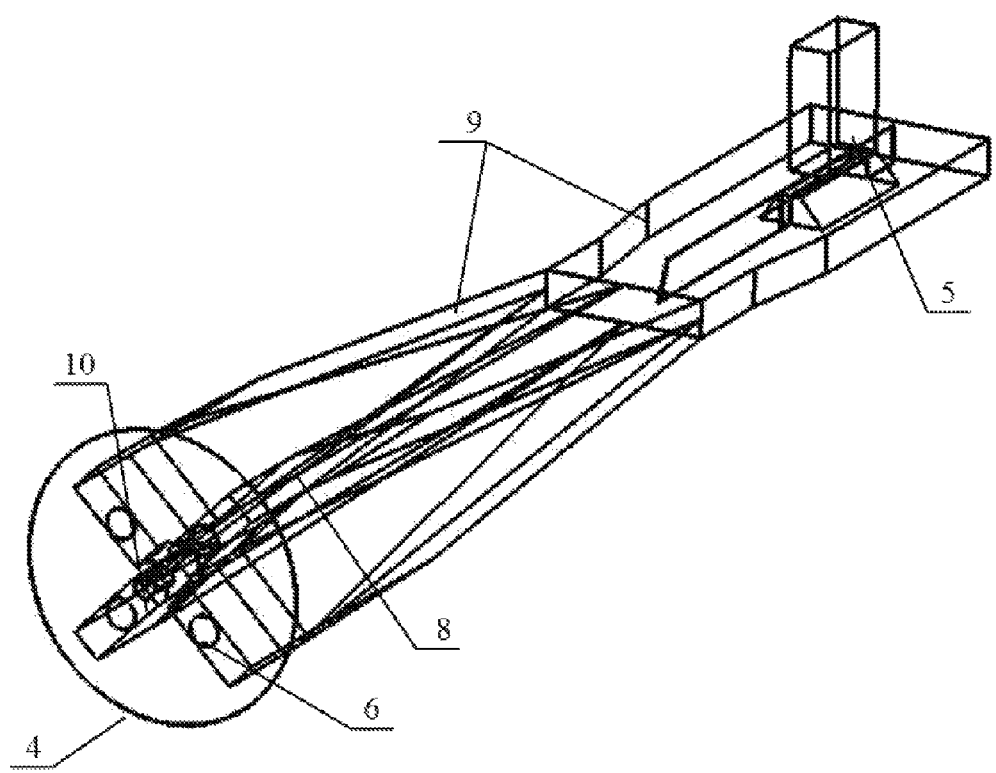
FIG. 4 is a schematic view showing transition from a standard rectangular waveguide section to the coaxial line of the coupling unit with four rectangular waveguide sections.

Waveguide sections 8 may be introduced for various purposes, for example, selection of modes in the coaxial waveguide 7 (an example is given in FIG. 3) or increasing the field concentration at the coupling holes 6 (an example is given in FIG. 4).

In addition to the diaphragm with the coupling holes 6 therein and the coaxial waveguide 7, the coupling unit contains a waveguide transition 9 from the coaxial waveguide 7 to the waveguide 5 of, as a rule, rectangular cross-section. The waveguide transitions 9 of different types can be used.

The waveguide 5 is used as a measuring waveguide. It is noted that any other waveguide that is suitable for measuring may be used as the measuring waveguide.

FIG. 3 and FIG. 4 show two examples of waveguide transitions realized in practice. FIG. 3 shows a half-section of a transition 9 from rectangular waveguide 5 to a coaxial waveguide 7 divided into waveguide sections 8. As a whole, the transition 9 consists of two mirror half-sections (FIG. 3). FIG. 4 shows a transition 9 consisting of a number of waveguide transitions, namely, a transition from rectangular waveguide 5 with $H_{10}$ mode to a rectangular waveguide with $H_{20}$ mode, a smooth transition from the rectangular waveguide with $H_{20}$ mode to a cross waveguide with $H_{20U}$ mode and a smooth transition from the cross waveguide with $H_{20U}$ mode to four waveguide sections 8 with $H_{10}$ modes.

The resonator comprises the resonating body 2 made of dielectric material and one or two flat bases 3 and 4. The whispering gallery modes can be excited in the resonators of various forms with the flat bases, for example, truncated cone, and hemisphere. As an example, FIG. 1 presents a case in which the dielectric body is a sapphire cylindrical disk.

Figure 5:
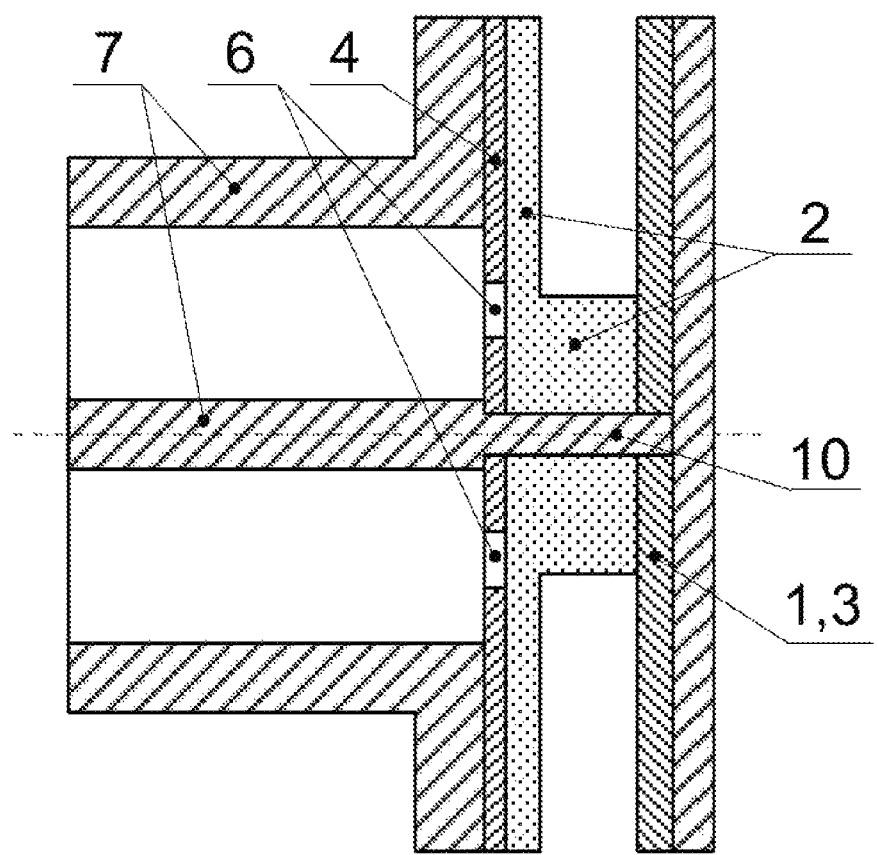
FIG. 5 is a general view of a measuring whispering-gallery-mode resonator according to another exemplary embodiment of the present invention.

In order to reduce losses, the diaphragm (the endplate 4) can be made of superconducting material. FIG. 5 shows an example of this idea. In this case the dielectric body 2 is formed by two sapphire disks, one of which (the left one having a larger diameter) is a substrate for the superconducting material (the endplate 4).

The resonator also includes a pin 10 for the installation of the resonating body 2 and electromagnetic shielding or absorbing material 11, with which a compartment surrounding the resonating body 2 is formed to protect the resonator from external influences. Though not shown, the resonator shown in FIG. 5 may similarly comprise the electromagnetic shielding or absorbing material.

Using the resonator of the present invention, one can study the material characteristics of the samples that differ in size and shape. The material and shape of the sample determine the specific structure of the resonator. For example, the endplate 3 in FIG. 5 defines the type of resonator (dielectric disk resonator with a conducting endplate) and, along with it, is the sample 1 of material with high conductivity.

In other cases, the sample 1 may be placed directly into the resonating body 2, for example, into the radial slot therein, as shown in FIG. 1. In this case, the endplate 3 of a material with high electrical conductivity will determine only the type and electrodynamic parameters of the resonator.

Measuring whispering-gallery-mode resonator works as follows.

In the resonating body 2 using a diaphragm (the endplate 4) with m holes, the whispering gallery mode is excited with azimuth index n=pm, where p=1, 2, .... The sample 1 under study causes change of the resonant frequency $f_0$ and the eigen Q-factor $Q_0$ of the resonator. The above mentioned changes are measured by the scheme "on reflection" at an arbitrary coupling coefficient β of the resonator with the coaxial waveguide 7. The coefficient β is selected according to the task, i.e. depending on the type of the sample 1 under study and the given temperature interval, where the microwave surface impedance $Z_S$ must be determined.

Consider a special case of measurement, namely, the measurement of the surface resistance $R_S$ of the sample under test 1 when endplate 3 is the sample 1 of high-temperature superconducting film under study. The inverse value of eigen Q-factor can be calculated as following:

$$Q_0^{-1} = A_S R_S + A_S^{(d)} R_S^{(d)} + k \tan \delta \quad (1)$$

where $A_S$ and $A_S^{(d)}$ are the coefficients of interaction of microwave field of the resonating body 2 with the sample 1 under study and the diaphragm (endplate 4) accordingly, $R_S$ and $R_S^{(d)}$ respectively indicate the surface resistances of the sample and the diaphragm (endplate 4), k is the coefficient of interaction of microwave field with the resonating body, tan δ is dielectric loss tangent of the resonating body. All of the above mentioned coefficients of interaction are determined by means of calibration procedure or calculated on the basis of solving the electrodynamic problem.

It is clear from (1) that a surface resistance equals $$R_S = (Q_0^{-1} - A_S^{(d)} R_S^{(d)} - k \tan \delta)/A_S \quad (2)$$

The eigen Q-factor $Q_0$ of the resonator is calculated by using measurement data of reflection coefficient for operative wave mode [V. V. Glamazdin, M. P. Natarov, V. N. Skresanov, A. I. Shubnyi, Radiation of local coupling elements of open resonators, *Telecommunications and Radio Engineering*. Vol. 71, No 10, 867-892, 2012]. For this purpose the replacing equivalent circuit of the resonator (FIG. 6) is used. Operating oscillation mode is modeled by a parallel resonant circuit of admittance $G_z + jB_z(f)$, where $G_z$ is a conductance of the oscillatory circuit, $B_z(f) = 2G_z Q_z \tau_z(f)$ is a reactive conductivity of the oscillatory circuit, which is proportional to the characteristic resistance $G_z Q_z$ and frequency mismatch (or detuning) $\tau_z(f) = (f - f_z)/f_z$, where $f_z$ and $Q_z$ are resonance frequency and Q-factor of the resonator. f is a running value of frequency. In turn, the active conductance $G_z$ is the sum of the conductance $G_0$ of the resonator in the absence of the coupling unit and conductance $G_x$ of the resonator including the coupling unit, that is, $G_z = G_0 + G_x$. With the conductivity $G_x$ additional losses of the resonator, namely, scattering the resonance field on the coupling unit into space is taken into account. Conductivity $G_0$ describes a sum of all other losses of the resonator including conductivity losses in the sample 1.

Measuring characteristics of the sample 1 under study with the resonator is carried out by comparison of Q-factors measured in the presence and absence of the sample 1 in the resonator. And in both cases, a power scattering by the coupling unit takes place. Therefore, to measure the losses introduced by the sample, knowledge of the scattering Q-factor of the coupling unit was not required. That is why next, we will continue to identify Q-factor $Q_z$ of the equivalent circuit and eigen Q-factor $Q_0$, so $Q_0 \equiv Q_z$.

At the same time, the presence of non-resonant losses in the coupling unit must be considered when calculating the eigen Q-factor $Q_0$. These losses are modeled by sequential impedance $Z_d = R_d + jX_d$ of the coupling unit (see FIG. 6). It is wrong, for example, to identify the coupling coefficient with a standing wave ratio in coaxial waveguide 7 or an inverse of a standing wave ratio, which though is true, as a rule, in a case of coupling unit of cavity resonator.

A modification of the impedance method of both measurement and calculation of the eigen Q-factor $Q_0$ of the resonator is proposed, which is as follows.

First, by using the network analyzer, the reflection coefficient $\Gamma(f)$ from the resonator is recorded.

Loaded Q-factor $Q_L$, resonance frequency $f_L$ and other parameters of the complex reflection coefficient of the resonator are found by approximation of squared modulus response, that is, $y(f) = |\Gamma(f)|^2$, where $$\Gamma(f) = \Gamma_d + \frac{A + jB}{1 + 2jQ_L t(f)} \quad (3)$$

$t(f) = (f - f_L)/f_L$ is frequency detuning parameter with respect to $f_L$; A and B are real and imaginary parts of the amplitudes of the waves reflected into a waveguide 7 from the resonator at the frequency $f_L$.

The eigen Q-factor and the eigen frequency $f_0$ can be calculated from the measured values $Q_L$, $f_L$, $\Gamma_d$, A, and B by the analytical formulas. These values are obtained by comparing the two expressions for the impedance $Z(f)$ of the resonator.

On one hand, the impedance $Z(f)$ is related to the reflection coefficient $\Gamma(f)$, and impedance $Z(f)$ is expressed as following:

$$Z(f) = \frac{1 + \Gamma(f)e^{j\Phi}}{1 - \Gamma(f)e^{j\Phi}} \quad (4)$$

where Φ is the phase of a reflection coefficient in the plane of representation of impedance $Z(f)$ relative to the reference plane of representation of the reflection coefficient $\Gamma(f)$.

Figure 6:
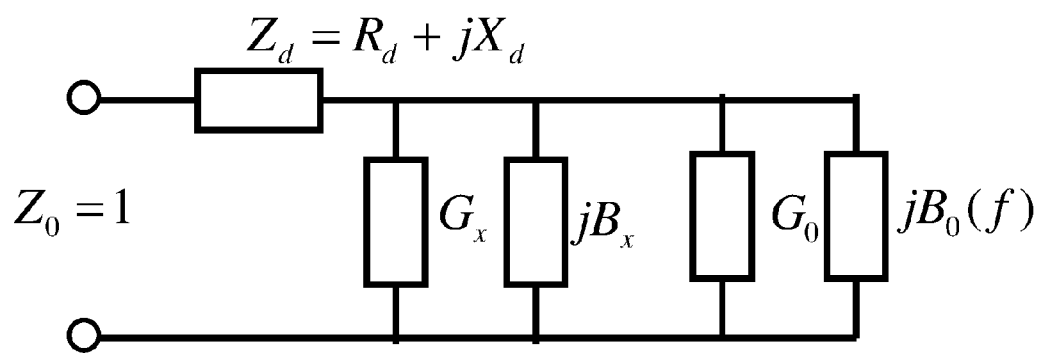
FIG. 6 is an equivalent circuit of a measuring whispering-gallery-mode resonator with one element of coupling.

On the other hand, the expression for the resonator impedance can be written as following by using the equivalent circuit of the resonator (FIG. 6)

$$Z(f) = Z_d + \frac{1/G_0}{1 + 2jQ_0 \tau_0(f)}, \quad (5)$$

where $\tau_0(f) = (f - f_0)/f_0 \approx t(f) - t_0$, $t_0 = (f_0 - f_L)/f_L$.
The following final relations are satisfied:

$$f_0 = f_L \left(1 + \text{Re}\left(\frac{1 - (\Gamma_d + A + jB)e^{j\Phi}}{2jQ_L(1 - \Gamma_d e^{j\Phi})}\right)\right), \quad (6)$$

and $$Q_0^{-1} = -\text{Im}\left(\frac{1 - (\Gamma_d + A + jB)e^{j\Phi}}{2jQ_L(1 - \Gamma_d e^{j\Phi})}\right),$$

where the unknown phase is a solution of the following trigonometric equation $$\sin(\Phi + \theta) = 2B\Gamma_d/C, \quad (7)$$

where $\sin(\theta) = B(1 + \Gamma_d^2)/C$, $C = \sqrt{(A(1 - \Gamma_d^2))^2 + (B(1 + \Gamma_d^2))^2}$.

Then one can also calculate all the characteristics of the coupling unit of interest, for example, the non-resonant loss of the coupling unit, which is characterized by efficiency of resonant oscillation excitation η equal to the ratio of power of its own losses $P_0$ in the resonator to the power transmitted through the coupling unit:

$$\eta = \frac{P_0}{P_{inc} - P_{ref}},$$

where $P_{inc}$ is the power incident from the waveguide 7 on the coupling unit, $P_{ref}$ is the power reflected from the resonator into the waveguide, or the coupling coefficient with a waveguide 7 $\beta = Q_0/Q_L - 1$.

Figure 7:
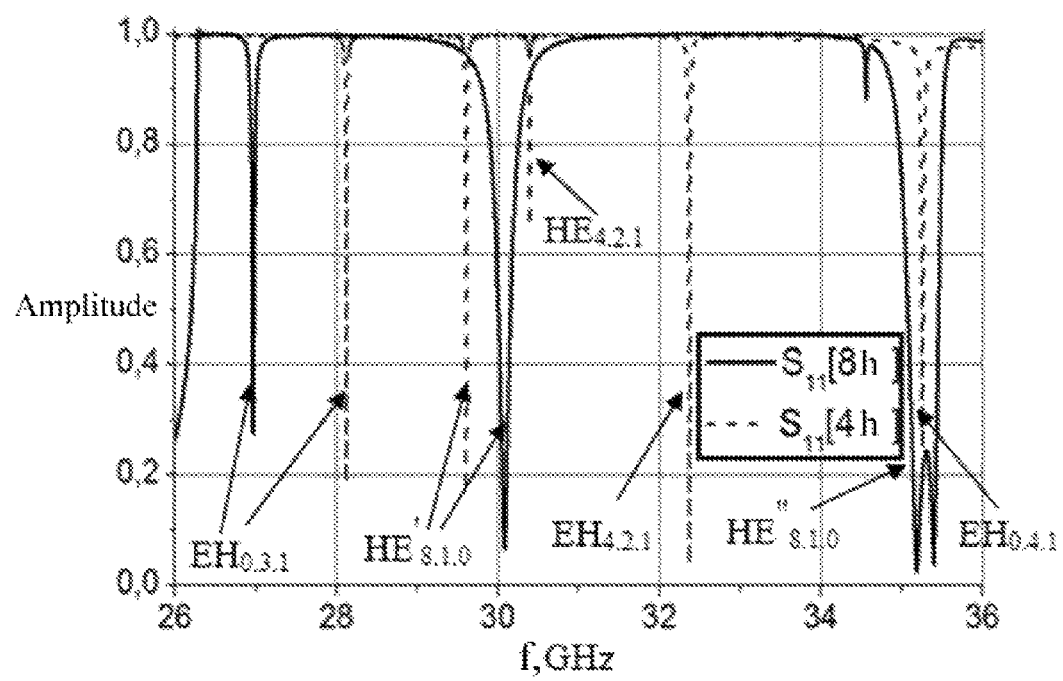
FIG. 7 shows the spectrum of the reflection coefficients of two measuring whispering-gallery-mode resonators, wherein the two resonators respectively have a high conductivity sample and a low conductivity sample, and are respectively provided with 4 coupling holes and 8 coupling holes.
Figure 8:
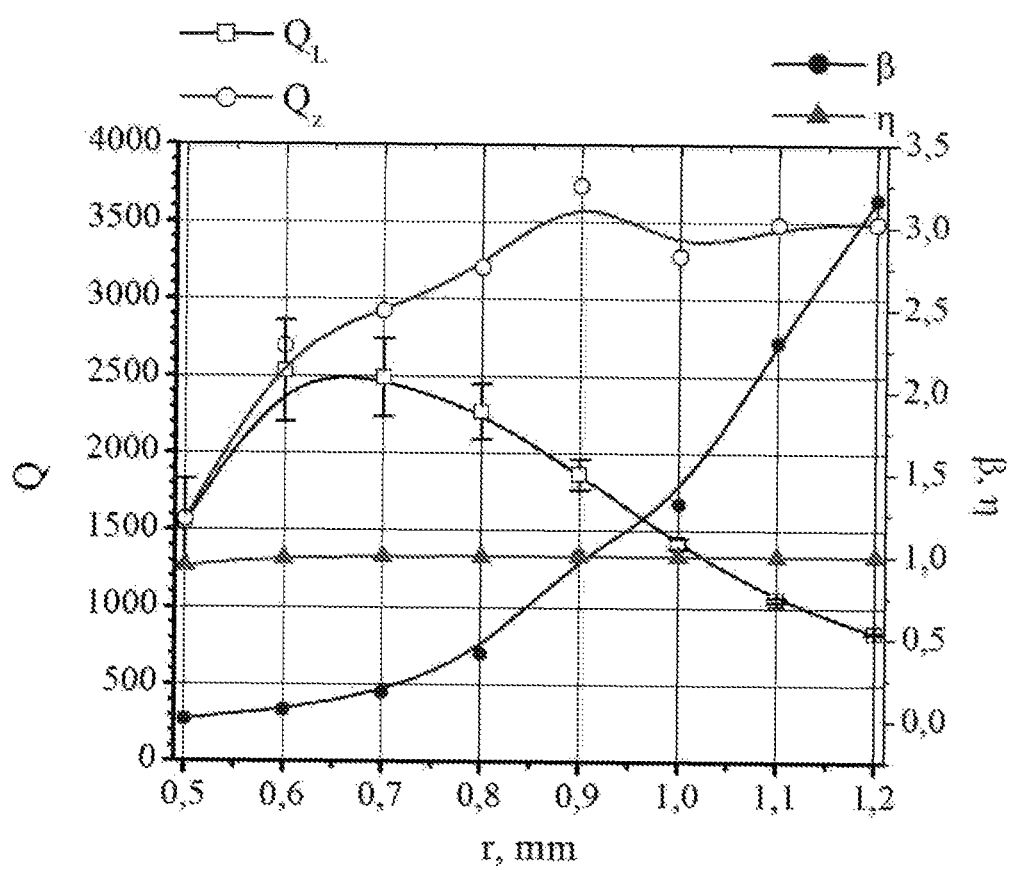
FIG. 8 shows an example of a coupling coefficient β, an efficiency of excitation η, a loaded Q-factor $Q_L$ and an eigen Q-factor $Q_0$ of a measuring whispering-gallery-mode resonator depending on hole radius $r=d_h/2$.

Dependencies in FIG. 7 and FIG. 8 show specific features of excitation method of the resonator with the endplates that are samples 1 under study by means of coaxial waveguide 7 through a system of the holes 6 in a thin diaphragm. Operation of all the coupling units presented in a given description is based on using $H_{01}$ mode excited in coaxial waveguide 7.

FIG. 7 shows the spectrum of the reflection coefficients of the measuring disk resonators with high- and low-conducting endplates (samples 1 under study) excited by 4 (indicated S11[4h] in FIG. 7) and 8 (indicated S11[8h] in FIG. 7) holes accordingly. The radius and height of the sapphire disk are respectively R=5.15 mm and L=2.5 mm Centers of coupling holes of diameter $d_h$=1.8 mm are located along a circle of a radius $R_h$=5 mm in a copper diaphragm of 0.2 mm thickness.

Both HE and EH modes can be excited in the resonators. The mode axial indices are closely related to number of the coupling holes in a diaphragm. From symmetry principle it is evidently, that periodicity of the resonator field variation along azimuth coordinate is equal to number of the coupling holes in a diaphragm or exceeds that by integer factor. As a result, selection of the resonator modes is observed. Number of excited modes decreases with increasing number of coupling holes, as can be seen in FIG. 7.

A disk sapphire resonator with $HE_{8,1,0}$ mode was designed at 30 GHz, and the modes were identified at the resonator excitation by means of diaphragm with 4 and 8 holes. Some modes are denoted in FIG. 7. Besides the mode selection, an attractive feature of the coupling unit is removal of polarization degeneration of operating $HE_{8,1,0}$ mode. It breaks up to two $HE'_{8,1,0}$ and $HE''_{8,1,0}$ modes with well different eigen frequencies.

Testing of the known coupling units for dielectric resonators with wave guides has shown that the excitation efficiency is about 50%. At the same time, the proposed coupling units show a high efficiency of excitation of whispering gallery modes.

FIG. 8 shows the dependence of the coupling coefficient β, the excitation efficiency η, and also the loaded $Q_L$ and eigen $Q_Z$ Q-factors of the sapphire disk resonator by 4 coupling holes whose centers are located along a circle of a radius $R_h$=5 mm in copper diaphragm of 0.2 mm thickness. The radius and height of the sapphire disk are R=5.15 mm, L=2.5 mm $HE'_{8,1,0}$ mode is used. As can be seen in FIG. 8, the efficiency of excitation is close to a hundred percent for all tested diameters of coupling holes 6.

The coupling coefficient β can optionally vary from very small values to the values several times greater than 1 by means of changing the diameter $d_h$=2r of the holes. A strong dependence on the radius $R_h$ is also observed, which determines centers of the coupling holes. The coupling coefficients close to critical can be obtained for the resonators with the samples 1 under study of both low conductivity and high conductivity (compare two curves in FIG. 7). This means the possibility of measuring the samples with significantly different electrophysical characteristics at high signal to noise ratio and in convenient dynamic range of changing the resonance curve.

Note one more feature inherent in all coupling units of measuring whispering gallery mode dielectric resonators. Changing the coupling coefficients by means of changing the geometric parameters of the coupling unit elements is accompanied by changes in both external and eigen Q-factors of the resonator. This feature remains valid for the proposed coupling units (see FIG. 8). Neglecting changes in eigen Q-factor of the resonators leads to systematic errors in the calculation of the electrophysical properties of sample 1 under study.

The proposed coupling unit for the resonator, in contrast to the known, allows the measurement on the signal reflected from the cavity. As shown, the mentioned possibility allows one to apply the impedance method of calculating the eigen Q-factor of the resonator, whose value becomes the known at any tuning of the coupling unit. Thus, this source of systematic (methodical) errors of electrical characteristics measurement of the samples under study is taken into account when carrying out research using the proposed resonator.

The solution of the present invention can be used in those sectors of the economy and science, where the microwave properties of substances, which are studied or measured, are basic and/or determine the characteristics of microwave devices developed on the basis of these substances. It can also be used, for example, to measure the microwave properties of superconductors, normal conductors and for non-contact monitoring of their conductivity. It can be used also in the development of the measuring cell in the spectrometers with electron-nuclear double resonance (ENDOR), where for the nuclear polarization it is necessary to use higher levels of electromagnetic radiation power in the THz range.

Although several exemplary embodiments have been shown and described, it would be appreciated by those skilled in the art that various changes or modifications may be made in these embodiments without departing from the principles and spirit of the disclosure, the scope of which is defined in the claims and their equivalents.

What is claimed is:

1. A measuring whispering-gallery-mode resonator, comprising:
   a dielectric resonating body with a rotation axis;
   a superconducting sample under test, which is mounted to the resonating body;
   a coupling unit for coupling a measuring waveguide with the resonating body,
   wherein one side of the resonating body connected with the coupling unit is provided with a first endplate, wherein m coupling holes penetrate through the first endplate, and centers of the m coupling holes are arranged to be evenly spaced along a circle whose said centers are on the rotation axis;
   the coupling unit has a feeder line which is a coaxial waveguide, wherein an axis of the coaxial waveguide coincides with the rotation axis, and one end surface of the coaxial waveguide, which is perpendicular to the rotation axis, abuts to the first endplate; and
   the azimuthal index n of operated whispering gallery mode $HE_{nkl}$ or $EH_{nkl}$ in the resonator is an integer multiple of the number m>1 of the coupling holes, wherein k≥1 and l≥0 are radial and axial indices, and the first endplate located between the coaxial waveguide and the dielectric resonating body has said m coupling holes.

2. The resonator according to claim 1, wherein
the first endplate is a diaphragm which is made of a high conducting material, and the first endplate is an element of the coupling unit.

3. The resonator according to claim 1, wherein
the sample under test forms a second endplate, which is arranged at the other side of the resonating body and parallel with the first endplate-diaphragm.

4. The resonator according to claim 1, wherein the resonating body is formed therein with a radial slot in which the sample under test is placed, wherein the radial slot is a groove along the entire height of the rotation axis and has a thickness equal to a thickness of the sample under test.

5. The resonator according to claim 4, further comprising an electromagnetic shielding or absorbing material which is provided between opposite radial outer edges of the first and second endplates so as to seal a chamber around the resonating body.

6. The resonator according to claim 1, wherein the resonating body comprises a first resonating section and a second resonating section which are formed integrally and whose rotation axes coincide with each other, wherein the first resonating section is formed as an endplate or substrate which is in surface contact with the first endplate, and the radius of the second resonating section is less than that of the first resonating section.

7. The resonator according to claim 1, wherein the coaxial waveguide is divided into m waveguide sections which have rotational symmetry of the m-th order; and
each waveguide section contains a corresponding coupling hole.

8. The resonator according to claim 7, wherein the coaxial waveguide is a cylindrical waveguide and comprises m waveguide sections which are divided by metal walls into m waveguide sections.

9. The resonator according to claim 7, wherein the measuring waveguide comprises a rectangular standard waveguide; and
the m waveguide sections comprises m rectangular waveguide sections.

10. The resonator according to claim 9, wherein the coupling unit further comprises a transition provided between the rectangular standard waveguide and the m rectangular waveguide sections.

11. The resonator according to claim 10, wherein said m coupling holes and said m waveguide sections respectively equals 4; and
the transition comprises a first transition from rectangular standard waveguide with $H_{10}$ mode to a rectangular waveguide with $H_{20}$ mode, a transition from the rectangular waveguide with $H_{20}$ mode to a cross waveguide with $H_{20U}$ mode and a transition from the cross waveguide with $H_{20U}$ mode to the m rectangular waveguide sections with $H_{10}$ modes.

* * * * *